(12) United States Patent
Tian et al.

(10) Patent No.: US 7,740,748 B2
(45) Date of Patent: Jun. 22, 2010

(54) ELECTROPHORESIS SYSTEM AND METHOD

(75) Inventors: Wei-Cheng Tian, Clifton Park, NY (US); Shashi Thutupalli, Bangalore (IN); Li Zhu, Clifton Park, NY (US); Anthony John Murray, Lebanon, NJ (US); Erin Jean Finehout, Clifton Park, NY (US); Jun Xie, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/258,657

(22) Filed: Oct. 27, 2008

(65) Prior Publication Data

US 2010/0101951 A1     Apr. 29, 2010

(51) Int. Cl.
*G01N 27/447* (2006.01)
*G01N 27/453* (2006.01)
(52) U.S. Cl. .................. 204/453; 204/604; 204/601; 204/451
(58) Field of Classification Search ......... 204/600–605, 204/451–455; 422/99, 100, 103
See application file for complete search history.

(56) References Cited

U.S. PATENT DOCUMENTS

| | | | |
|---|---|---|---|
| 4,879,247 A | | 11/1989 | Ohlson |
| 4,908,112 A | * | 3/1990 | Pace ................... 210/198.2 |
| 5,077,017 A | | 12/1991 | Gorin et al. |
| 5,644,395 A | | 7/1997 | Folta |
| 5,824,204 A | * | 10/1998 | Jerman ................ 204/601 |
| 5,976,336 A | | 11/1999 | Dubrow et al. |
| 6,010,607 A | | 1/2000 | Ramsey |
| 6,056,859 A | * | 5/2000 | Ramsey et al. ........... 204/451 |
| 6,210,986 B1 | * | 4/2001 | Arnold et al. ............. 438/42 |

(Continued)

FOREIGN PATENT DOCUMENTS

EP     0268406 A2     11/1987

(Continued)

OTHER PUBLICATIONS

F. Lacharme et al, "Pressure Injection in Continuous Sample Flow Electrophoresis Microchips", Sensors &L Actuators B: Chemical, vol. 117, Issue 2, Oct. 12, 2006, pp. 1-19.

(Continued)

*Primary Examiner*—Alex Noguerola
(74) *Attorney, Agent, or Firm*—Jenifer E. Haeckl

(57) ABSTRACT

Electrophoresis systems and methods comprise an electrophoresis device, wherein the electrophoresis device comprises a loading channel, an injection channel, and a separation channel. The loading channel is in fluid communication with a first and second sample port. The injection channel is connected to the loading channel to form a first intersection. The separation channel is connected to the injection channel to form a second intersection and in fluid communication with a first and second reservoir, and wherein the injection channel is in fluid communication with a third reservoir. The electrophoresis system further comprises electrodes coupled to the first sample port and the third reservoir, and the first reservoir and the second reservoir, respectively, that are adapted to move the sample into the loading channel towards the third reservoir and form a sample plug in the second intersection, and to further move the sample plug into the separation channel towards the second reservoir.

18 Claims, 3 Drawing Sheets

U.S. PATENT DOCUMENTS

| | | | |
|---|---|---|---|
| 6,251,343 B1 | 6/2001 | Dubrow et al. | |
| 6,432,290 B1 * | 8/2002 | Harrison et al. | 204/453 |
| 7,005,050 B2 | 2/2006 | Burns et al. | |
| 7,214,298 B2 | 5/2007 | Spence et al. | |
| 2001/0035351 A1 | 11/2001 | Simpson et al. | |
| 2002/0197736 A1 | 12/2002 | Amirkhanian | |
| 2003/0215855 A1 | 11/2003 | Dubrow et al. | |
| 2003/0230486 A1 | 12/2003 | Chien et al. | |
| 2004/0195099 A1 | 10/2004 | Jacobson et al. | |
| 2005/0006238 A1 * | 1/2005 | Jaffe | 204/450 |
| 2006/0042948 A1 | 3/2006 | Santiago et al. | |
| 2006/0169588 A1 | 8/2006 | Jacobson et al. | |

FOREIGN PATENT DOCUMENTS

| | | |
|---|---|---|
| WO | 96/04547 A1 | 2/1996 |
| WO | 99/34220 A2 | 7/1999 |
| WO | WO9966318 | 12/1999 |
| WO | WO0131322 | 5/2001 |
| WO | WO0170397 | 9/2001 |
| WO | WO03084629 | 10/2003 |
| WO | WO2005118138 | 12/2005 |

OTHER PUBLICATIONS

Y. Lin et al., "A Poly-methyomethacrylate Electrophoresis Microchip with Sample Preconcentrator", J. Micromech., Microeng. 11 (2001), pp. 1.89-194.

R Ma. et al, "A Rapid Performance Assessment Method for Microfluidic Chips", Proceedings of the 2004 International Conf. on MEMS, NANO and Smart Systems, 2004 IEEE, pp. 1-7.

R. Schlund et al., "Continuous Sampling and Analysis by On-Chip Liquid/Solid Chromatography", Sensors & Actuators: B, Chemical, vol. 123, No. 2, 2007 pp. 1-2.

R. Johann et al., "A Simple Mechanism for Reliable Particle Sorting in a Microdevice With Combined Electroosmotic and Pressure-Driven Flow", Electrophoresis 2004, 25, pp. 3720-3729.

D. Huh, et al., "Microfluidics for Flow Cytometric Analysis of Cells and Particles", Physiol. Meas. 26 (2005) R-73-R98.

Pei Yu Chiou, Aaron T.Ohta and Ming C. Wu; "Massively parallel manipulation of single cells and microparticles using optical images"; Nature 436, 370-372 (Jul. 21, 2005) | doi: 10.1038/nature03831.

P.F. Man, D.K. Jones and C.H. Mastrangelo; "Microfluidic Plastic Capillaries on Silicon Substrates: A New Inexpensive Technology for Bioanalysis Chips"; Center for Integrated Sensors and Circuits, Department of Electrical Engineering and Computer Science, University of Michigan, Ann Arbor, MI 48109-2122, USA; 0-7803-3744-1/97/$5.00 0 1997 IEEE; on pp. 311-316.

* cited by examiner

ELECTROPHORESIS SYSTEM AND METHOD

BACKGROUND

This invention relates generally to an electrophoresis system and a method for performing microfluidic manipulation. More particularly, this invention relates to a microfluidic chip and a method for introducing sample for electrophoretic separation.

Electrophoresis is widely used analytical techniques in chemical and biological research, such as DNA sequencing, protein analysis and genetic mapping. The term electrophoresis refers to a process in which charged molecules are separated in a given separation medium, such as an electrolyte solution under influence of an electric filed. The charged molecules migrate through the separation medium and separate into distinct bands due to different mobilities within the separation medium.

A variety of electrophoresis apparatus have been commercially available for analysis of a sample. One such type of the electrophoresis apparatus is a capillary electrophoresis apparatus. The capillary electrophoresis can be considered as one of the latest and most rapidly expanding techniques in analytical chemistry. It refers to a family of related analytical techniques that uses electric fields to separate molecules within narrow-bore capillaries (typically 20-100 um internal diameter) or within channels of a microfluidic device.

In a standard microfluidic capillary electrophoresis device, the sample is introduced into a sample reservoir connected to an injection channel. Due to concerns of contamination by carry-over, the sample reservoir can only be used for a single sample. One can have multiple reservoirs, each connected to the injection channel, but due to the small size of most microfluidic devices, you are limited in the number of reservoirs that can fit on a single device. Therefore one is often faced with the tradeoff of either making a more compact (and thus cheaper) device or making a larger device and being able to analyze a greater number of samples per chip.

It is possible to have the injection channel of an electrophoresis directly connected with a capillary or channel where the sample is flowing through. The challenge is the pressure will force some of the sample into the injection channel, pushing back the electrolyte medium that is disposed within. One solution that has been proposed is having a deep mixing channel connected to the injection channel. The deep and narrow mixing channel introduces additional steps (and thus costs) into the fabrication in order to have channels of varying depth on the same device.

Therefore, there is a need for a new and improved system and method for performing microfluidic manipulation and introducing a sample into an electrophoresis device.

BRIEF DESCRIPTION

An electrophoresis system in accordance with one embodiment of the invention is provided. The electrophoresis system comprises an electrophoresis device. The electrophoresis device comprises a loading channel, an injection channel, and a separation channel. The loading channel is in fluid communication with a first and second sample port. The injection channel is connected to the loading channel to form a first intersection. The separation channel is connected to the injection channel to form a second intersection and in fluid communication with a first and second reservoir, and wherein the injection channel is in fluid communication with a third reservoir. The electrophoresis system further comprises electrodes coupled to the first sample port and the third reservoir, and the first reservoir and the second reservoir, respectively, that are adapted to move the sample into the loading channel towards the third reservoir and form a sample plug in the second intersection, and to further move the sample plug into the separation channel towards the second reservoir.

An electrophoresis device in accordance with another embodiment of the invention is provided. The electrophoresis device comprises a loading channel, an injection channel, and a separation channel. The loading channel is in fluid communication with a first and second sample port. The injection channel is connected to the loading channel to form a first intersection. The separation channel is connected to the injection channel to form a second intersection and in fluid communication with a first and second reservoir, and wherein the injection channel is in fluid communication with a third reservoir.

A method for controlling the flow of one or more fluids in an electrophoresis device in accordance with another embodiment is provided. The electrophoresis device comprises a loading channel, an injection channel, and a separation channel. The loading channel is in fluid communication with a first and second sample port. The injection channel is connected to the loading channel to form a first intersection. The separation channel is connected to the injection channel to form a second intersection and in fluid communication with a first and second reservoir, and wherein the injection channel is in fluid communication with a third reservoir. Further, the method comprises the steps of loading one or more of a buffer solution and a sieving matrix into the separation channel and the injection channel from one or more of the first and second sample ports and the first and the second reservoir, loading the sample into the loading channel from one of the first and the second sample port, applying a first potential electrically coupled to the first sample port and the third reservoir to move the sample into the loading channel towards the third reservoir and form a sample plug in the second intersection, and applying a second potential electrically coupled to the first reservoir and the second reservoir to move the sample plug into the separation channel towards the second reservoir.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE DISCLOSURE

Figure 1:
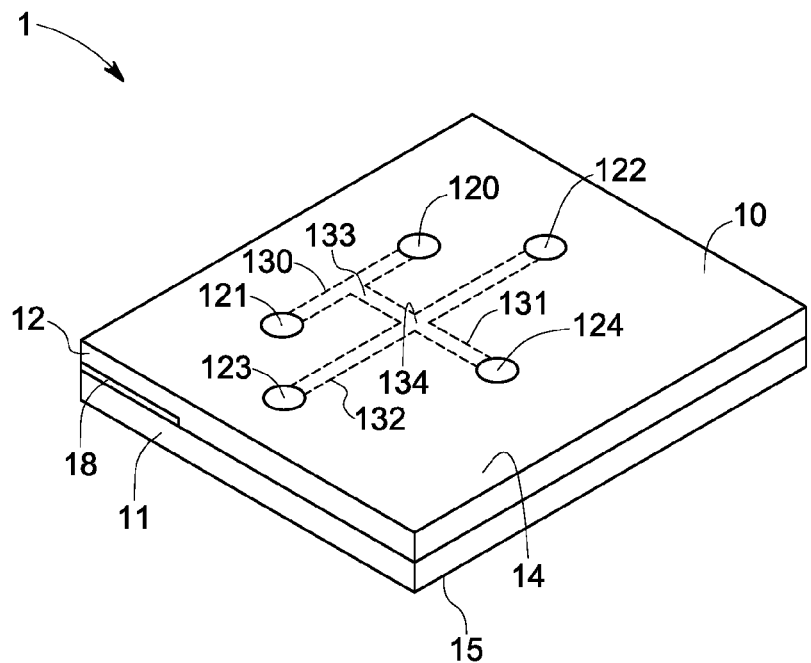
FIG. 1 is a schematic diagram of an electrophoresis system with a channel subsystem in accordance with one embodiment of the invention.

FIG. 1 illustrates a schematic diagram of an electrophoresis system with a channel subsystem in accordance with one embodiment of the invention. As illustrated in FIG. 1, an electrophoresis system 1 comprises an electrophoresis apparatus 10 comprising a substrate 11 and a cover 12 attached on a surface of the substrate 11. In certain embodiments of the invention, the electrophoresis apparatus 10 may be a microfluidic chip. And the substrate 11 and the cover 12 may be made of glass, silicon, or other materials known in the semiconductor arts, or of a suitable polymer material, such as plastic.

Generally, a microfluidic chip, also referred to as a lab-on-a-chip or a microchip, is a miniaturized device for manipulating and analyzing chemical/biological samples in micrometer-sized channels. The microfluidic chip may comprise a chemical/biological microprocessor for use in a variety of processes, such as, but not limited to, injection, separation and detection, integrated in a glass, silicon, plastic or other suitable substrate having an area of several square centimeters. It offers faster analysis while using much smaller amount of samples and reagents, usually on a micro-liter or nano-liter scale.

In the illustrated embodiment, the microfluidic chip 10 defines a channel subsystem 13, which is etched, micromachined or otherwise established therein. In one example, the channel subsystem 13 is fabricated by techniques from semiconductor manufacturer, such as photolithography etc. The channel subsystem 13 comprises a loading channel 130, an injection channel 131, and a separation channel 132 each disposing in the substrate 11. In one or more embodiments, the loading channel 130 is wider than the injection channel 131 and the separation channel 132. The injection channel 131 is in fluid communication with the loading channel 130 at one end thereof to form a first intersection 133. And the separation channel 132 is in fluid communication with the injection channel 131 to form a second intersection 134. In the illustrated embodiment, the second intersection 134 is formed in a cross-T configuration. Alternatively, the second intersection 134 may be formed in a single-T, double-T, or double-L configuration, which is known to one skilled in the art.

Additionally, the channel subsystem 13 comprises a first sample port 120, a second sample port 121, a first reservoir 122, a second reservoir 123, and a third reservoir 124 each passing through the cover 12. In this example, the first sample port 120 and the second sample port 121 communicate with two opposite ends of the loading channel 130, respectively. The first reservoir 122 and the second reservoir 123 are in fluid communication with two opposite ends of the separation channel 132. The third reservoir 124 is in fluid communication with another end of the injection channel 131 generally located at an end opposite to the end that is in fluid communication with loading channel 130. In one example embodiment, the first intersection 133 is located between the first and second sample ports 120 and 121, and is adjacent, or otherwise in close proximity, to the first sample port 120. That is, the injection channel 131 is adjacent to the first sample port 120.

Alternatively, in other embodiments of the invention, the cover 12 may be formed with the loading channel 130 recessed upward from a lower surface thereof to communicate with the injection channel 131. Additionally, the microfluidic chip 10 may further comprise a middle element 18, such as a gasket or a glass plate disposed between the substrate 11 and the cover 12. In this example, the loading channel 130 may be defined in the middle element 18 to communicate with the injection channel 131. The first and second sample ports 120 and 121 may pass through the cover 12 and the middle element 18 to communicate with the loading channel 130.

Further, the loading channel 130 may pass through the substrate 11 and the cover 12 vertically. The first sample port 120 and the second sample port 121 may be located on an upper surface 14 (shown in FIG. 1) of the cover 12 and a lower surface 15 (shown in FIG. 1) of the substrate 11, respectively. This configuration may minimize a dead/swept volume of the sample, and reduce a pressure drop across the loading channel.

In one or more of the embodiments of the invention, the loading channel 130 is used for loading a sample from the first sample port 120 or the second sample port 121 using various pressure driven methods. In one example, when using a positive pressure to push the sample into the loading channel 130, the second sample port 121 may be used as a sample inlet on which the positive pressure is exerted. When using a negative pressure to draw the sample into the loading channel 130, the first sample port 120 can be used as the sample inlet, and the negative pressure is exerted on the second sample port 121. Thus, reducing influence of the loading pressure to the injection channel 131 and the separation channel 132. Accordingly, the first sample port 120 or the second sample port 121 may be used as a sample outlet. Additionally, the injection channel 131 is for receiving a part of the sample from the loading channel 130 to form a sample plug in the second intersection 134. The separation channel 132 is used for receiving the sample plug for separation.

In one or more embodiments of the invention, the first reservoir 122 and/or the second reservoir 123 may be used as buffer reservoirs and/or sieving matrix reservoirs for injecting a buffer solution and/or a sieving matrix into the channel subsystem 13. The second reservoir 123 may also be used as a separation waste reservoir to receive the separation waste from the separation channel 132. The third reservoir 124 may be used as a waste sample reservoir to receive the waste sample from the injection channel 131. The first and second sample ports 120 and 121 may also be used for injection of a buffer solution and/or a sieving matrix. In one or more embodiments of the invention, the buffer solution may comprise tris-HCl and sodium dodecyl sulfate and the sieving matrix may comprise a polyethylene oxide.

Figure 2A:
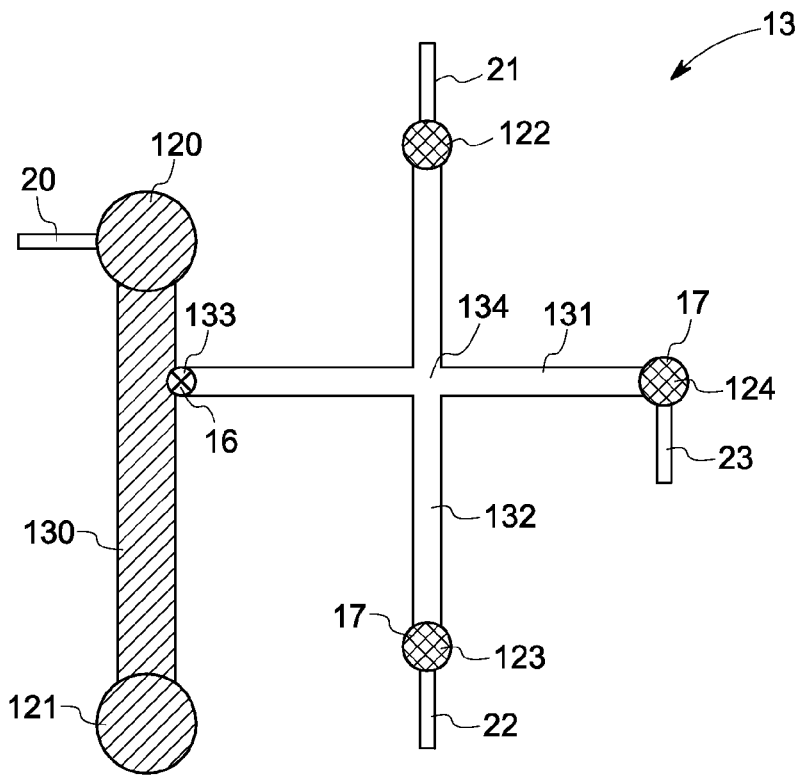
FIGS. 2(a)-2(d) are schematic flow diagrams of steps for injecting and separating a sample in accordance with one embodiment of the invention.

FIGS. 2(a)-2(d) are schematic flow diagrams of an example embodiment of the steps for injecting and separating a sample. As illustrated in FIG. 2(a), the electrophoresis system 1 further comprises a first electrode 20 disposed in the first sample port 120, a second electrode 21 disposed in the first reservoir 122, a third electrode 22 disposed in the second reservoir 123, and a fourth electrode 23 disposed in the third reservoir 124. In one or more embodiments, the electrodes may be disposed detachably within the respective sample ports and reservoirs. Alternatively, the electrodes may be integrated into the microfluidic chip.

In the illustrated embodiment, during operation, at least one of a first buffer solution and a first sieving matrix may be transported into all the channels in advance from at least one of the first sample port 120, the second sample port 121, the first reservoir 122, the second reservoir 123, and the third reservoir 124. In one embodiment, at least one of the first buffer solution and the first sieving matrix may be injected into the injection channel 131 and the separation channel 132 in advance from the second reservoir 123 (separation waste reservoir). In certain embodiments, when injecting both the first buffer solution and the first sieving matrix, the first sieving matrix may be filled into the separation channel 132 behind the second intersection 134 from the second reservoir 123. In one example, after injecting the first sieving matrix into the injection channel 131 and the separation channel 132 from the second reservoir 123, the first and third reservoirs 122 and 124 may also be filled with the sieving matrix.

Next, referring to FIG. 2(a), in this example, the sample is pressure loaded into the channel 130 from the first sample port 120 or the second sample port 121. In one embodiment, the buffer solution or the sieving matrix may be employed to pretreat the sample before the sample is loaded in the loading channel 130.

Figure 2B:
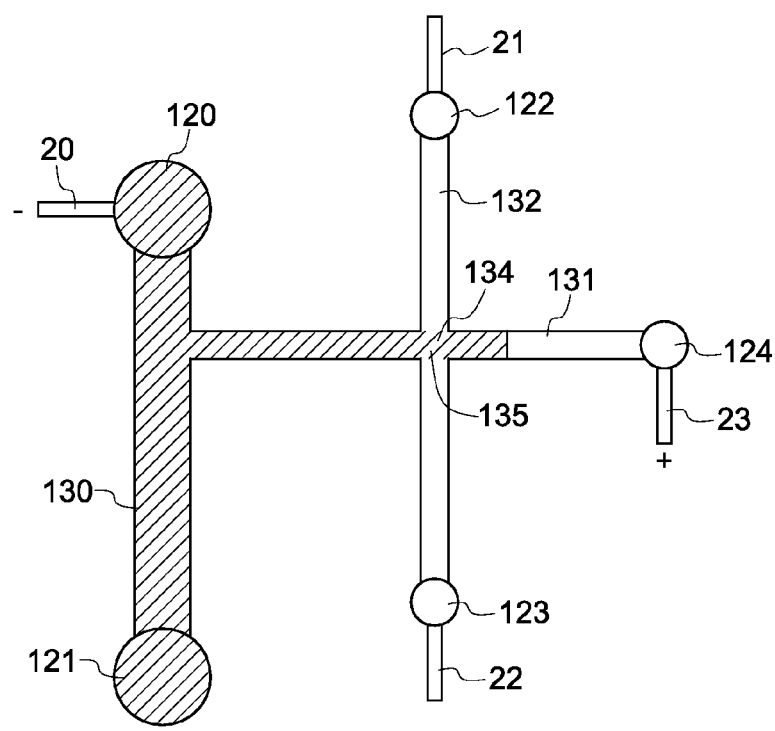

Referring to FIG. 2(b), a first potential is applied to the first electrode 20 and the fourth electrode 23 while a floating voltage is applied to the second electrode 21 and the third electrode 22. In the illustrated embodiment, the first electrode 20 and the fourth electrode 23 are applied with a negative potential and a positive potential, respectively. Thus, a part of the sample in the loading channel 130 is electro-kinetically transported into the injection channel 131 to form a sample plug 135 in the second intersection 134. To ensure that the composition of the sample in the sample plug 135 reflects the actual sample composition in the loading channel 139, the electrical field across the first electrode 20 and the fourth electrode 23 must be maintained for a sufficient period of time.

Figure 2C:
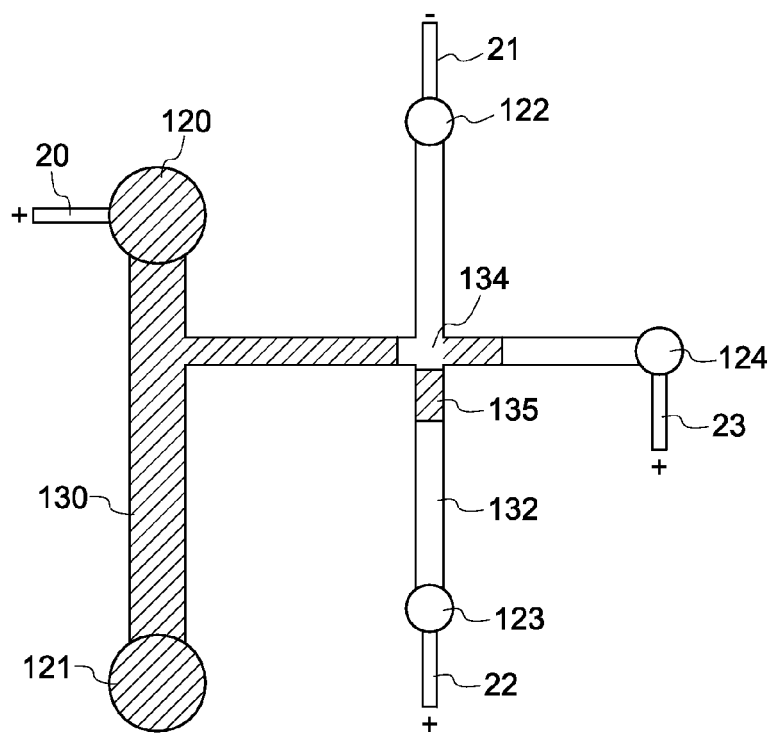

Following this, as illustrated in FIG. 2(c), a second potential is applied to the second electrode 21 and the third electrode 22. In this example, the second electrode 21 and the third electrode 22 are applied with a negative potential and a positive potential, respectively. Accordingly, the sample plug 135 is transported into the separation channel 132 after the second intersection 134 for separation. In the meantime, the first electrode 20 and the fourth electrode 23 may also be applied with positive potentials, to cooperate with the second electrode 221, to pull the sample in the injection channel 131 backward and forward towards the loading channel 130 and the third reservoir 124, respectively.

Alternatively, while transporting the sample into the injection channel 131 and the sample plug 135 into the separation channel 132, respectively, the first electrode 20 and the second electrode 21 may be grounded, respectively, while positive potential(s) are applied to the other electrode(s). Additionally, negative potentials and grounding potentials may also be cooperatively applied to the electrodes.

Figure 2D:
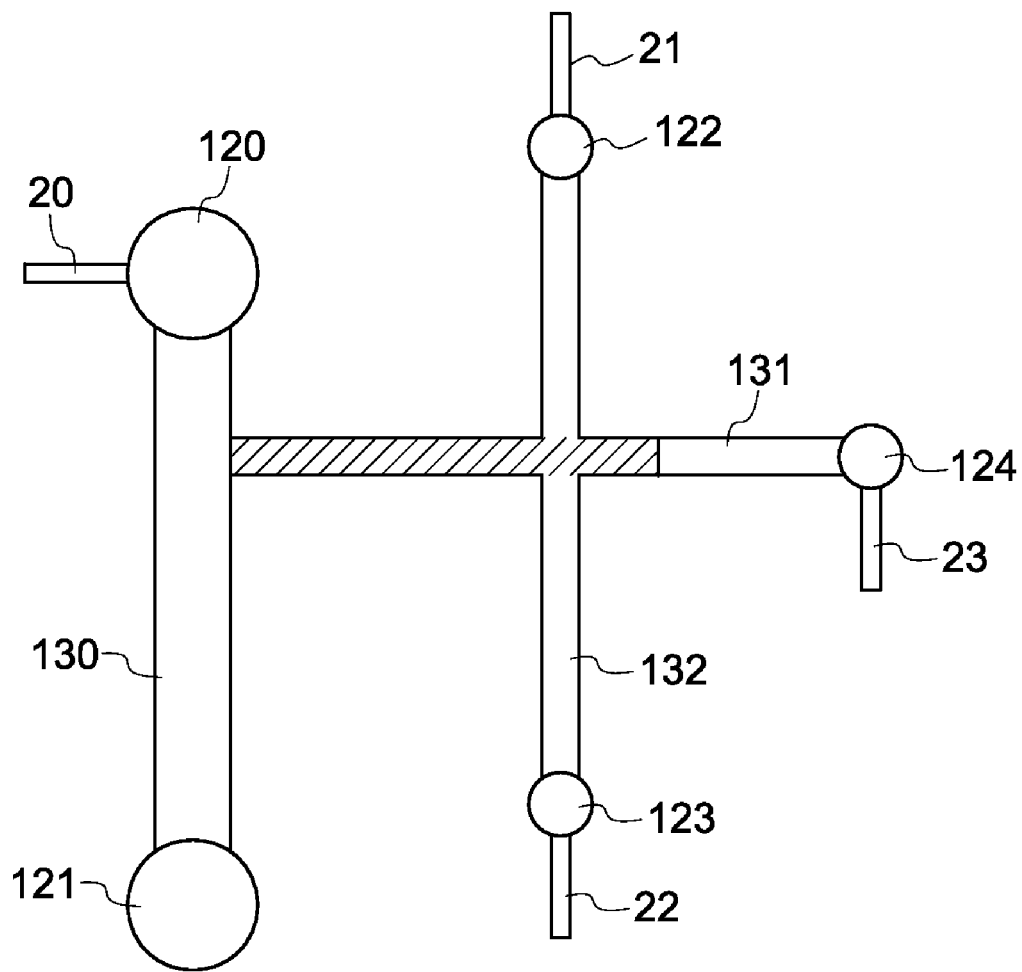

In one embodiment, as illustrated in FIG. 2(d), after forming the sample plug 135 in the second intersection 134 and before separating the sample plug 135 in the separation channel 132, the potentials across the first and fourth electrodes 20 and 23 may be shut off, and a second buffer solution or a second sieving matrix same as or similar to the first buffer solution or first sieving matrix, respectively, may be injected into the loading channel 130 to rinse away the sample therein.

Referring again to FIG. 2(a), in this example embodiment of the invention, the sample is pressure-loaded into the loading channel 130. Therefore, during loading, the loading pressure of the sample may push the buffer solution, and/or the sieving matrix back in the injection channel 131 to cause the subsequent flow of the sample. In addition, the loading channel may drive the sample to enter the injection channel 131 while loading to cause cross-contamination.

As described above, the first intersection 133 may be adjacent, or otherwise in close proximity, to the first sample port 120. In one or more embodiments, by selecting the first sample port 120 or the second sample port 121 to be the sample inlet based on different pressure driven methods, the influence of the loading pressure on the injection channel 131 and the separation channel 132 may be reduced. Additionally, in one or more of the embodiments, the flow resistance ratio of the loading channel 130 and the injection channel 131 may be suitably varied to reduce or otherwise alter the effect of the loading pressure.

Generally, a flow resistance 'R' of a microfluidic channel depends on its geometry and fluid properties. Assuming that a microfluidic channel has a height 'H', a width 'W' and a length 'L', and carries a fluid with a viscosity 'η', the flow resistance of the microfluidic channel may be expressed by the following equation:

$$R \cong \frac{12\eta L}{1 - 0.63 \ (H/W)} \frac{1}{H^3 W}$$

As shown in the above equation, increasing the length and/or the width of the microfluidic channel will increase and reduce the flow resistance 'R', respectively.

Therefore, in one or more of the embodiments of the invention, the injection channel 131 may have a longer length and a smaller width than the length and width of the loading channel 130 to reduce the influence of the loading pressure on the injection channel 131 and the separation channel 132. However, as the length of the injection channel 131 is increased, the requisite injection time of the sample may increase as well. As such, the required high flow resistance ratio and the desired injection time can be adapted to suit a given application. In one example embodiment, the width of the loading channel 130 is about 200 um or more and the width of the injection channel 131 is about 20-50 um.

In certain embodiments, besides increasing flow resistance difference between the loading channel 130 and the injection channel 131, as illustrated in FIG. 2(a), a valve 16 may be disposed in the first intersection 133 so that the injection channel 131 may be closed while loading, and opened after loaded. The valve 16 may comprise an elastomer membrane pressure driven valve, such as, for example, the valve disclosed in U.S. Pat. No. 5,593,130, or a sliding linear valve disclosed in U.S. Pat. No. 6,870,185. Other suitable on-chip valves may also be used.

As illustrated in FIG. 2(a), the electrophoresis system 1 may comprise several covering elements 17 disposed on the first, second and third reservoirs 122-124. Thus, while loading the sample in the loading channel 130, the covering elements 17 may close the first, second and third reservoirs 122-124 to increase the pressure in the injection channel 131 and the separation channel 132 to offset a portion of the loading pressure, thereby reducing the effect of the loading pressure.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. An electrophoresis system, comprising:
an electrophoresis device comprising:
a microfluidic chip having a cover and a substrate, said substrate carrying three channels of approximately equal depth, said channels being:
a loading channel in fluid communication with and extending between a first and second sample port and having a width between four and ten times that of the other two channels,
an injection channel initiating at the loading channel to form a first intersection and in fluid communication with and terminating in a third reservoir,
a separation channel connected to the injection channel to form a second intersection and in fluid communication with and extending between a first and second reservoir;
electrodes coupled to the first sample port and the third reservoir, and the first reservoir and the second reservoir, respectively, that are adapted to move the sample into the loading channel towards the third reservoir and form a sample plug in the second intersection, and to further move the sample plug into the separation channel towards the second reservoir; and
means for applying a pressure differential between said first and said second sample port.

2. The electrophoresis system of claim 1, further comprising a valve disposed in the first intersection to generate flow resistance difference between the loading channel and the injection channel.

3. The electrophoresis system of claim 1, wherein the loading channel has a width of about 200 microns or more.

4. The electrophoresis system of claim 1, wherein the injection channel has a width between about 20 microns and 50 microns.

5. The electrophoresis system of claim 1, wherein the electrophoresis device comprises a microfluidic chip comprising a substrate formed with the loading channel, injection channel and the separation channel, and a cover coupled to the substrate and formed with the first sample port and the first, second and third reservoirs.

6. An electrophoresis system, comprising:
a microfluidic electrophoresis device comprising:
a chip having a cover and a substrate and carrying three channels, said channels being:
a loading channel passing vertically through said cover and substrate to provide a first sample port on the top of said cover and a second sample port on the bottom of said substrate,
an injection channel initiating at the loading channel to form a first intersection and in fluid communication with and terminating at a third reservoir,
a separation channel connected to the injection channel to form a second intersection and in fluid communication with and extending between a first and second reservoir; and
electrodes coupled to the first sample port and the third reservoir, and the first reservoir and the second reservoir, respectively, that are adapted to move the sample into the loading channel towards the third reservoir and form a sample plug in the second intersection, and to further move the sample plug into the separation channel towards the second reservoir.

7. The electrophoresis system of claim 5, wherein the second sample port is disposed in the cover.

8. The electrophoresis system of claim 5, wherein the second sample port is disposed in the substrate.

9. The electrophoresis system of claim 6, wherein the cover is formed with the first, second and third reservoirs.

10. An electrophoresis device, comprising:
a microfluidic chip having a cover and a substrate and carrying three channels, said channels being:
a loading channel in fluid communication with and extending between a first and second sample port;
an injection channel initiating at to the loading channel to form a first intersection; and in fluid communication with and terminating at a third reservoir; and
a separation channel connected to the injection channel to form a second intersection and in fluid communication with and extending between a first and second reservoir;
wherein either
all three channels are formed in the substrate and are of approximately equal depth and the loading channel has a width of between about four and ten times that of the other two channels; or
the loading channel passes vertically through said cover and substrate to provide a first sample port on the top of said cover and a second sample port on the bottom of said substrate; and
means for creating a pressure differential between said first and said second sample port.

11. The electrophoresis device of claim 10, wherein when the loading channel is of approximately equal depth with the other two channels it has a width of about 200 microns or more.

12. The electrophoresis device of claim 10, wherein the electrophoresis device comprises a microfluidic chip comprising a substrate formed with the loading channel, injection channel and the separation channel, and a cover coupled to the substrate and formed with the first sample port and the first, second and third reservoirs.

13. The electrophoresis device of claim 12, wherein the injection loading channel has a width between about 20 microns and 50 microns.

14. The electrophoresis device of claim 12, wherein the second sample port is disposed in the cover.

15. The electrophoresis device of claim 12, wherein the second sample port is disposed in the substrate.

16. A method for controlling the flow of one or more fluids in an electrophoresis device, comprising the steps of:
providing an electrophoresis device comprising:
a microfluidic chip having a cover and a substrate and carrying three channels, said channels being:
a loading channel in fluid communication with and extending between a first and second sample port,
an injection channel initiating at the loading channel to form a first intersection and in fluid communication with and terminating at a third reservoir, and
a separation channel connected to the injection channel to form a second intersection and in fluid communication with and extending between a first and second reservoir, and wherein the injection channel is in fluid communication with a third reservoir;
wherein either
all three channels are formed in the substrate and are of approximately equal depth and the loading channel has a width of between about four and ten times that of the other two channels; or
the loading channel passes vertically through said cover and substrate to provide a first sample port on the top of said cover and a second sample port on the bottom of said substrate;
loading one or more of a buffer solution and a sieving matrix into the injection channel and the separation channel from one or more of the first and second sample ports, and the first, second and third reservoirs;

loading a sample into the loading channel from one of the first and second sample ports by applying a pressure differential between said sample ports;

applying a first potential electrically coupled to the first sample port and the third reservoir to move the sample into the injection channel towards the third reservoir and form a sample plug in the second intersection; and applying a second potential electrically coupled to the first reservoir and the second reservoir to move the sample plug into the separation channel towards the second reservoir.

17. The method of claim 16, further comprising a step of providing a valve disposed in the first intersection for closing the injection channel while loading the sample into the loading channel and for opening the injection channel after loading the sample into the loading channel.

18. The method of claim 16, further comprising a step of shutting off the first potential and rinsing away the sample in the loading channel after the step of forming the sample plug in the second intersection.

* * * * *